(12) United States Patent
Menabde et al.

(10) Patent No.: US 9,706,902 B2
(45) Date of Patent: Jul. 18, 2017

(54) OBJECTIVE LENS FOR ENDOSCOPIC DEVICE, ACTUATOR FOR FOCUSING, AND ENDOSCOPIC SYSTEM

(75) Inventors: Sergey Menabde, Suwon-si (KR); Jong-chul Choi, Suwon-si (KR); Hae-in Chung, Uijeongbu-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 901 days.

(21) Appl. No.: 13/529,086

(22) Filed: Jun. 21, 2012

(65) Prior Publication Data
US 2013/0137930 A1    May 30, 2013

(30) Foreign Application Priority Data

Nov. 28, 2011  (KR) .......... 10-2011-0125311

(51) Int. Cl.
*G02B 15/14*  (2006.01)
*A61B 1/00*   (2006.01)
*G02B 23/24*  (2006.01)

(52) U.S. Cl.
CPC ........ *A61B 1/00096* (2013.01); *G02B 23/243* (2013.01)

(58) Field of Classification Search
USPC ........................................... 359/676
See application file for complete search history.

(56) References Cited

U.S. PATENT DOCUMENTS

| | | | |
|---|---|---|---|
| 4,037,938 A | 7/1977 | Yamashita et al. | |
| 5,587,839 A | 12/1996 | Miyano et al. | |
| 5,936,778 A | 8/1999 | Miyano et al. | |
| 5,971,915 A | 10/1999 | Yamamoto et al. | |
| 6,084,715 A | 7/2000 | Aoki et al. | |
| 6,327,101 B1 | 12/2001 | Miyano | |
| 6,404,453 B1 * | 6/2002 | Yoshikawa | B41J 2/345 347/200 |
| 6,404,563 B1 | 6/2002 | Wildy | |
| 6,524,235 B2 | 2/2003 | Mitsumori | |
| 6,537,208 B1 | 3/2003 | Konno | |
| 6,956,703 B2 | 10/2005 | Saito | |
| 7,180,686 B2 | 2/2007 | Kato | |
| 7,379,252 B2 | 5/2008 | Murayama | |
| 7,466,490 B2 | 12/2008 | Igarashi | |

(Continued)

FOREIGN PATENT DOCUMENTS

| CN | 1941120 | 4/2007 |
|---|---|---|
| CN | 1957836 | 5/2007 |

(Continued)

OTHER PUBLICATIONS

Extended European Search Report dated Mar. 14, 2013 issued in EP Application No. 12193611.6.

(Continued)

*Primary Examiner* — Jack Dinh

(74) *Attorney, Agent, or Firm* — Staas & Halsey LLP

(57) ABSTRACT

An objective lens for an endoscope, an actuator for focusing the objective lens, and an endoscope system including the objective lens are provided. The objective lens for an endoscope includes a plurality of lenses and a stop, and an optical element disposed adjacent to the stop, wherein a focal length may be varied by moving the optical element in a direction different from an optical axis.

32 Claims, 13 Drawing Sheets

(56) References Cited

U.S. PATENT DOCUMENTS

| | | |
|---|---|---|
| 7,486,449 B2 | 2/2009 | Miyano |
| 7,522,209 B2 | 4/2009 | Wakashiro |
| 7,764,437 B2 | 7/2010 | Yamamoto |
| 7,828,721 B2 | 11/2010 | Kumei et al. |
| 7,871,371 B2 | 1/2011 | Komiya et al. |
| 8,395,850 B2 | 3/2013 | Tashiro |
| 2001/0007511 A1 | 7/2001 | Minami et al. |
| 2008/0180809 A1 | 7/2008 | Igarashi |
| 2009/0067067 A1 | 3/2009 | Yamaya |
| 2009/0237807 A1 | 9/2009 | Sasamoto |
| 2010/0097707 A1* | 4/2010 | Seo ................ G02B 15/173 359/672 |
| 2010/0277638 A1 | 11/2010 | Craven-Bartle |
| 2010/0305405 A1 | 12/2010 | Miyano |
| 2011/0002052 A1 | 1/2011 | Nasu |

FOREIGN PATENT DOCUMENTS

| | | |
|---|---|---|
| CN | 101877763 | 11/2010 |
| JP | 49-11146 | 1/1974 |
| JP | 60-23814 | 2/1985 |
| JP | 6-317745 | 11/1994 |
| JP | 2000-33015 | 11/2000 |
| JP | 2008-107391 | 5/2008 |
| JP | 2010-286819 | 12/2010 |
| JP | 2011-144338 | 7/2011 |
| RU | 2270416 | 2/2006 |
| WO | 2013/002019 | 1/2013 |

OTHER PUBLICATIONS

"High-resolution and high-magnification endoscopes", Gastrointestinal Endoscopy, vol. 69, No. 3, 2009, pp. 399-407.
"GI endoscopes", Gastrointestinal Endoscopy, vol. 74, No. 1, 2011, pp. 1-12.
Chinese Office Action dated Mar. 17, 2016 in Chinese Patent Application No. 201210494979.3.
Japanese Office Action dated Aug. 2, 2016 in Japanese Patent Application No. 2012-204854.
Chinese Office Action dated Oct. 11, 2016 in Chinese Patent Application No. 20121049479.3.
Russian Office Action dated Dec. 7, 2016 in Russian Patent Application No. 2012150914/28.
Russian Notice of Allowance dated Mar. 21, 2017 in Russian Patent Application No. 2012150914/28.

* cited by examiner

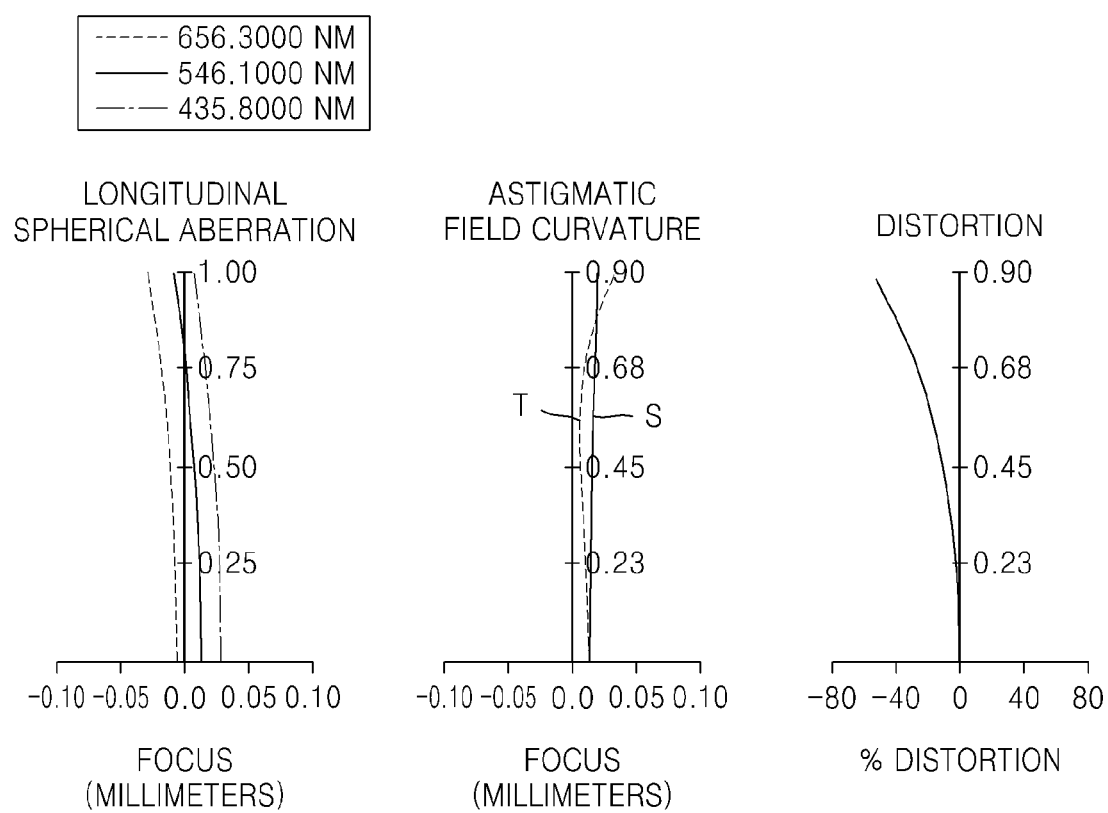

OBJECTIVE LENS FOR ENDOSCOPIC DEVICE, ACTUATOR FOR FOCUSING, AND ENDOSCOPIC SYSTEM

CROSS-REFERENCE TO RELATED APPLICATION(S)

This application claims priority from and the benefit under 35 U.S.C. §119 to Korean Patent Application No. 10-2011-0125311, filed on Nov. 28, 2011, in the Korean Intellectual Property Office, the disclosure of which is incorporated herein in its entirety by reference.

BACKGROUND

1. Field

The present general inventive concept relates to an objective lens of a digital photographing apparatus, an actuator for focusing the objective lens, and an endoscope including the objective lens.

2. Discussion of the Background

Endoscopy is widely used in medical examination, diagnosis, and treatment of patients with internal organ problems. Endoscopy allows patients to recover fast after a procedure, and also offers doctors great flexibility when conducting surgical or other procedures. Thus, endoscopy is generally used in various types of hospitals and clinics.

Endoscopy apparatuses have been gradually developed in recent years. For example, an imaging unit has been developed from a fiber optic image guide for using a digital sensor. An objective lens has been developed to meet the demands of modern image sensors. Although a lens structure of an objective lens of an endoscope may be simple, the size of an endoscope is limited.

Recently, new image quality standards for endoscopes have been introduced. The maximum effective image resolution option has increased from 0.3 megapixels (MP) to 1.3 MP or higher. High image quality is important for the medical staff to view the affected area clearly. Since a size of an imaging unit is limited, a sensor size has remained constant, and to provide a possibility of obtaining the mentioned resolution, a pixel size has been reduced. However, with smaller pixel sizes (high resolution), it is difficult to obtain a wide depth of field (DOF) due to diffraction limitations.

In addition, to perform focusing with an objective lens used in an endoscope, at least one lens is moved along an optical axis. However, this operation increases a size of a lens system, a driving mechanism for moving a lens is complicated, and a control system therefor is also complicated. Moreover, a focusing system as described above may be inconvenient to use due to a short DOF at a near distance.

SUMMARY

The present general inventive concept provides an objective lens for an endoscope, which may be focused using a simple and cost-effective method.

The present general inventive concept also provides an actuator for focusing an objective lens for an endoscope.

The present general inventive concept also provides an endoscope system that is cost-effective and has excellent focusing performance.

Additional features and utilities of the present general inventive concept will be set forth in part in the description which follows and, in part, will be obvious from the description, or may be learned by practice of the general inventive concept.

According to an exemplary embodiment of the present general inventive concept, there is provided an objective lens for an endoscope comprising; a plurality of lenses; a stop; and an optical element disposed adjacent to the stop, wherein a focal length of the objective lens is variable according to a movement of the optical element in a direction different from an optical axis of the plurality of lenses.

The movement of the optical element is between a position on the optical axis and a position deviated from the optical axis.

The optical element may be a non-power transparent element.

The optical element may be a glass plate having two planar surfaces.

The optical element may have a positive refractive power or a negative refractive power.

The movement of the optical element may be in a direction perpendicular to the optical axis of the plurality of lenses.

The objective lens may include a front lens group having a negative refractive power, the stop, a rear lens group having a positive refractive power, and the optical element may be disposed between the front lens group and the stop or between the stop and the rear lens group.

An F-number Fno of the objective lens may be in a range from 4 to 6.

A depth of field (DOF) of the objective lens may be in a range from 5 mm to 100 mm at a far distance, and a DOF of the objective lens may be in a range from 2.5 mm to 10 mm at a near distance.

An aperture of the stop may be constant.

According to an exemplary embodiment of the present general inventive concept, there is provided an objective lens for an endoscope, comprising, sequentially from an object side of the objective lens, a front lens group having a negative refractive power, a stop, a rear lens group having a positive refractive power, and an optical element disposed between the front lens group and the stop or between the stop and the rear lens group, wherein the optical element is moveable in a direction different from an optical axis to focus the objective lens, and the front lens group includes a first lens having a negative refractive power and a second lens having a positive refractive power, and the rear lens group includes a third lens having a positive refractive power, a fourth lens having a positive refractive power, and a fifth lens having a negative refractive power, wherein the objective lens satisfies the following equation:

$$0.8 \leq |d_s/f_{G1}| \leq 1.8 \qquad \text{<Equation>}$$

where $d_s$ denotes a distance between a vertex of the first lens at the object side and the stop, and $f_{G1}$ denotes a focal length of the front lens group.

The second lens may be a meniscus type lens having a convex surface disposed toward an image side of the objective lens.

The objective lens may satisfy the following equation:

$$d_{48}/f_{fr} \geq 2.0 \qquad \text{<Equation>}$$

where $d_{48}$ denotes a distance between a vertex of the second lens at an image side of the objective lens and a vertex of the third lens at the object side of the objective lens, and $f_{fr}$ denotes a total focal length of the objective lens.

The fourth lens and the fifth lens may be cemented together.

The objective lens may satisfy the following equation:

$$f_2/f_{fr} \geq 6.0$$

$$0.3 \leq f_{45}/f_2 \leq 2.5 \qquad \text{<Equation>}$$

where $f_2$ denotes a focal length of the second lens, and $f_{fr}$ denotes a total focal length of the objective lens, and $f_{45}$ denotes a focal length of the cemented fourth lens and fifth lens.

The second lens and the third lens may include aspherical surfaces.

According to exemplary embodiments of the present general inventive concept, there is provided an actuator for moving an optical element to perform focusing of an objective lens for an endoscope, comprising: a moveable holder to support the optical element; at least one guide hole formed in the holder; at least one guide shaft disposed in the at least one guide hole to guide a movement of the holder; and a driving unit to move the holder.

According to exemplary embodiments of the present general inventive concept, there is provided an endoscope system comprising: a bending portion having a terminal end; an objective lens disposed at the terminal end of the bending portion; and an inserting portion connected to the bending portion at an end of the bending portion opposite the terminal end, wherein the objective lens includes a plurality of lenses, a stop, and an optical element disposed adjacent to the stop, and a focal length of the objective lens is variable according to a movement the optical element in a direction different from an optical axis of the plurality of lenses.

According to exemplary embodiments of the present general inventive concept, there is provided an objective lens for an endoscope, the objective lens including a front lens group having a negative refractive power; a rear lens group having a positive refractive power; a stop disposed between the front and rear lens group; and an optical element disposed between the front lens group and the stop or between the stop and the rear lens group, the optical element being moveable in a direction different from an optical axis of the front lens group and the rear lens group.

The front lens group, sequentially from an object side of the objective lens, may further include a first lens having a negative refractive power and a second lens having a positive refractive power.

The second lens may be a meniscus type lens having a convex surface disposed toward an image side of the objective lens.

The rear lens group, sequentially from an object side of the objective lens, may further include a third lens having a positive refractive power, a fourth lens having a positive refractive power, and a fifth lens having a negative refractive power.

The second lens and the third lens may include aspherical surfaces.

The rear lens group, sequentially from an object side of the objective lens, may further include a third lens having a positive refractive power, a fourth lens having a positive refractive power, and a fifth lens having a negative refractive power.

The fourth lens and the fifth lens may be cemented together.

The optical element may be a non-power transparent element.

The optical element may be a glass plate having two planar surfaces.

The optical element may have a positive refractive power or a negative refractive power.

The optical element may include a meniscus shape having a convex surface disposed toward an object side of the objective lens.

According to exemplary embodiments of the present general inventive concept, there is provided an endoscope system comprising: a bending portion having a terminal end; an objective lens disposed at the terminal end of the bending portion; and an inserting portion connected to the bending portion at an end of the bending portion opposite the terminal end, wherein the objective lens comprises, sequentially from an object side of the objective lens, a front lens group having a negative refractive power, a stop, a rear lens group having a positive refractive power, and an optical element disposed between the front lens group and the stop or between the stop and the rear lens group, wherein the optical element is moveable in a direction different from an optical axis to focus the objective lens, and the front lens group includes a first lens having a negative refractive power and a second lens having a positive refractive power, and the rear lens group includes a third lens having a positive refractive power, a fourth lens having a positive refractive power, and a fifth lens having a negative refractive power, wherein the objective lens satisfies the following equation, $$0.8 \leq |d_s/f_{G1}| \leq 1.8 \qquad \text{<Equation>}$$

where ds denotes a distance between a vertex of the first lens at the object side and the stop, and fG1 denotes a focal length of the front lens group.

The endoscope system may satisfy the following equation:

$$f_2/f_{fr} \geq 6.0$$

$$0.3 \leq f_{45}/f_2 \leq 2.5 \qquad \text{<Equation>}$$

where $f_2$ denotes a focal length of the second lens, and $f_{fr}$ denotes a total focal length of the objective lens, and $f_{45}$ denotes a focal length of a doublet lens including the fourth lens and the fifth lens.

In the endoscope system, a depth of field (DOF) of the objective lens may be in a range from 5 mm to 100 mm at a far distance, and a DOF of the objective lens may be in a range from 2.5 mm to 10 mm at a near distance.

The foregoing and/or other features and utilities of the present general inventive concept may also be achieved by providing an objective lens usable with an endoscope, the objective lens including a front lens group having a negative refractive power, a rear lens group having a positive refractive power, a stop disposed between the front and rear lens group, and an optical element disposed between the front lens group and the stop or between the stop and the rear lens group, the optical element being moveable in a direction different from an optical axis of the front lens group and the rear lens group. The front lens group, sequentially from an object side of the objective lens, may include a first lens having a negative refractive power and a second lens having a positive refractive power.

The second lens may be a meniscus type lens having a convex surface disposed toward an image side of the objective lens.

The rear lens group, sequentially from an object side of the objective lens, may include a third lens having a positive refractive power, a fourth lens having a positive refractive power, and a fifth lens having a negative refractive power.

The second lens and the third lens may include aspherical surfaces.

The rear lens group, sequentially from an object side of the objective lens, may include a third lens having a positive refractive power, a fourth lens having a positive refractive power, and a fifth lens having a negative refractive power.

BRIEF DESCRIPTION OF THE DRAWINGS

These and/or other features and utilities of the present general inventive concept will become apparent and more readily appreciated from the following description of the embodiments, taken in conjunction with the accompanying drawings of which:

FIG. 3B illustrates aberrations when the objective lens of FIG. 1 for an endoscope performs focusing on a near object;

DETAILED DESCRIPTION OF THE ILLUSTRATED EMBODIMENTS

Figure 1:
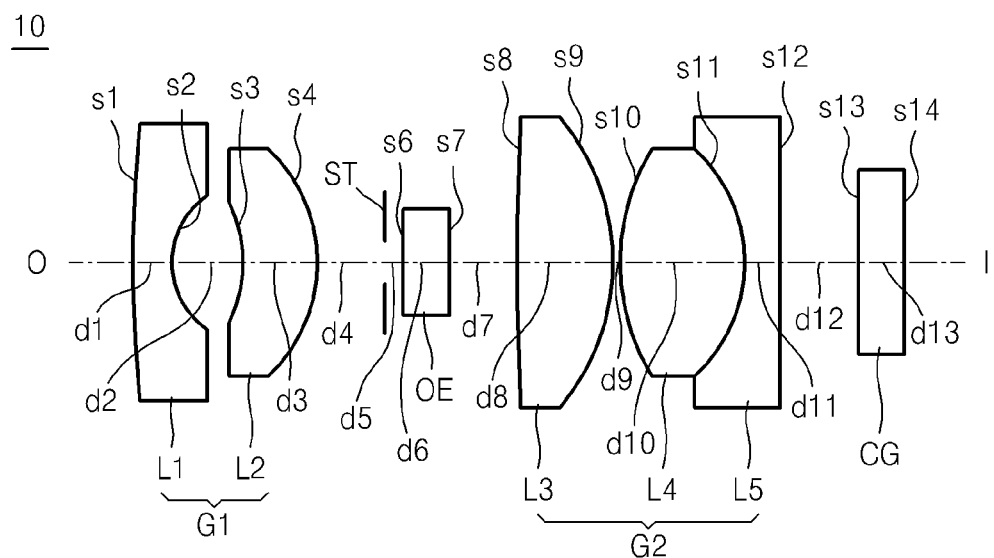
FIG. 1 is a cross-sectional view of an objective lens for an endoscope according to exemplary embodiments of the present general inventive concept.

Reference will now be made in detail to exemplary embodiments of the present general inventive concept, examples of which are illustrated in the accompanying drawings, wherein like reference numerals refer to the like elements throughout. These exemplary embodiments are described below in order to explain the present general inventive concept while referring to the figures.

Referring to FIG. 1, an objective lens 10 for an endoscope according to exemplary embodiments of the present general inventive concept includes a front lens group G1, a stop ST, and a rear lens group G2, which are sequentially disposed from an object side O. An optical element OE may be disposed adjacent to the stop ST. The optical element OE may be disposed, for example, between the front lens group G1 and the stop ST or between the stop ST and the rear lens group G2. The optical element OE is movable in a direction different from an optical axis, and focusing may be performed by using the optical element OE. The stop ST may be a fixed stop with a constant aperture. Thus, according to the objective lens 10 for an endoscope, an amount of light passing through the aperture may be constant.

Figure 2A:
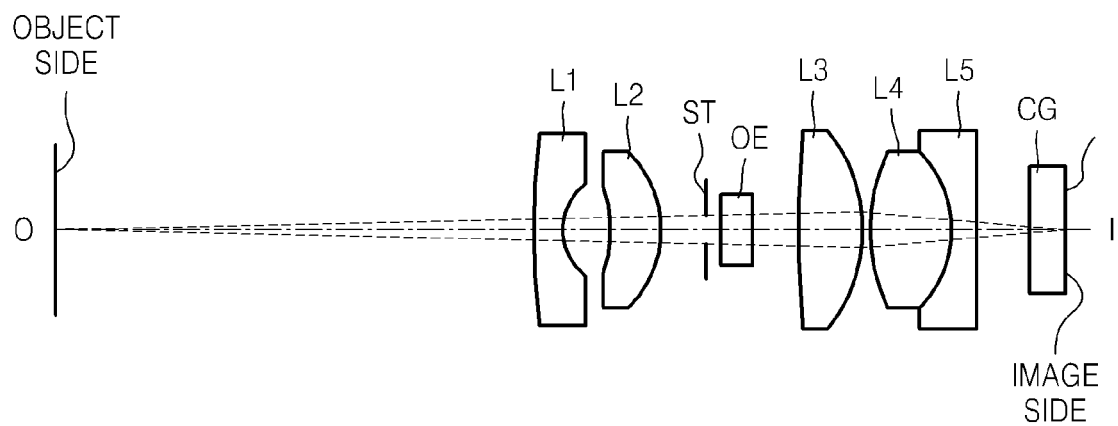
FIG. 2A illustrates focusing performed using the objective lens of FIG. 1 on a distant object.
Figure 2B:
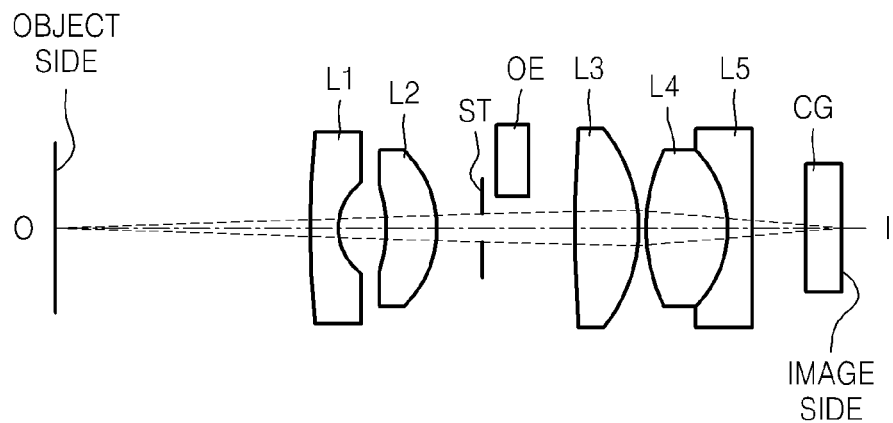
FIG. 2B illustrates focusing performed using the objective lens of FIG. 1 on a near object.

When the optical element OE is arranged on the optical axis as illustrated in FIG. 2A, a focal length is increased, and when the optical element OE is moved to deviate from the optical axis as illustrated in FIG. 2B, a focal length may be shortened. The optical element OE may be, for example, a non-power transparent element. Here, power refers to refractive power. When the optical element OE is a non-power device, an increase in costs due to the optical element OE is small, and total power of the objective lens is not affected, and thus, aberrations may be controlled easily, and the optical element OE may be moved with a high degree of freedom. However, the optical element OE is not limited thereto, and may also be a power element. In other words, the optical element OE may have a positive refractive power or a negative refractive power.

When the optical element OE is disposed adjacent to the stop ST, the optical element OE moves a small distance corresponding to an aperture of the stop ST, and thus an increase in a size of the objective lens 10 due to movement of the optical element OE may be small.

As described above, the optical element OE of the objective lens 10 for an endoscope may be moved in a direction different from the optical axis, for example, in a direction perpendicular to the optical axis, to adjust a focal length and obtain a high resolution image. For example, the objective lens 10 for an endoscope may have an F-number Fno in a range from 4 to 6. Also, a depth of field (DOF) of the objective lens 10 at a far distance may be in a range from 5 mm to 100 mm, and a DOF of the objective lens 10 at a near distance may be in a range from 2.5 mm to 10 mm. As there is an overlapping section in the ranges of the DOF at the far distance and the DOF at the near distance as above, a clear near-distance image having a high resolution may be captured.

Since the optical element OE is a non-power element, a degree of freedom of movement of the optical element OE is high so that focusing may be performed as the optical element OE is on the optical axis or deviates from the optical axis. Also, for focusing, movement of the optical element OE is not limited in a direction perpendicular to the optical axis and the optical element OE may also move at at least one angle. As sensitivity of the optical element OE is small, the optical element OE may be easily manufactured, and the manufacturing costs thereof may be low. The optical element OE may be formed of a glass plate. At least one surface of the glass plate may be planar. For example, a surface of the optical element OE may be stepped, and in this case a focal length may vary in various steps.

Referring to FIG. 1, the front lens group G1 may have a negative refractive power. The front lens group G1 may include a first lens L1 having a negative refractive power and a second lens L2 having a positive refractive power. The rear lens group G2 may have a positive refractive power. The rear lens group G2 may include a third lens L3 having a positive refractive power, a fourth lens L4 having a positive refractive power, and a fifth lens L5 having a negative refractive power. A cover glass CG may be further included at an image side I of the rear lens group G2.

The second lens L2 may be a meniscus type having a convex surface toward the image side I. The second lens L2 and the third lens L3 may be aspherical lenses. Also, the fourth lens L4 and the fifth lens L5 may be cemented.

In FIG. 1, distances d1-d13 are marked. Distance d1 is a distance between surfaces of the first lens L1 along the optical axis. Distance d2 is a distance between adjacent surfaces of the first lens L1 and the second lens L2 along the optical axis. Distance d3 is a distance between surfaces of the second lens L2 along the optical axis. Distance d4 is a distance between adjacent surfaces of the second lens L2 and the stop ST along the optical axis. Distance d5 is a distance between adjacent surfaces of the stop ST and the optical element OE along the optical axis. Distance d6 is a distance between surfaces of the optical element OE along the optical axis. Distance d7 is a distance between adjacent surfaces of the optical element OE and the third lens L3 along the optical axis. Distance d8 is a distance between surfaces of the third lens L3 along the optical axis. Distance d9 is a distance between adjacent surfaces of the third lens L3 and the fourth lens L4 along the optical axis. Distance d10 is a distance between surfaces of the fourth lens L4 along the optical axis. Distance d11 is a distance between surfaces of the fifth lens L5 along the optical axis. Distance d12 is a distance between adjacent surfaces of the fifth lens L5 and the cover glass CG along the optical axis. Distance d13 is a distance between surfaces of the cover glass CG along the optical axis.

Meanwhile, the objective lens 10 for an endoscope may satisfy the following Equation 1.

$$0.8 \leq |d_s/f_{G1}| \leq 1.8 \qquad \text{<Equation 1>}$$

where $d_s$ denotes a distance between a vertex of a surface of the first lens L1 at the object side O and the stop ST, i.e., $d_s = d1+d2+d3+d4$, and $f_{G1}$ denotes a focal length of the front lens group G1. If equation 1 is satisfied, the entire size of the objective lens 10 may be decreased. The size of the objective lens 10 may be determined by a size of the optical element OE and sizes of lenses, and these sizes may be related to a position of the stop ST. In order to keep a sufficient height of light rays on a lens surface, the stop ST may be disposed at about a middle point between the first lens L1 and the third lens L3. Also, in order to decrease or minimize the size of the optical element OE, the optical element OE may preferably be disposed as near to the stop ST as possible. Accordingly, a lower limit of Equation 1 defines a minimum size of the rear lens group G2, and an upper limit of Equation 1 defines a minimum size of the front lens group G1. That is, by satisfying Equation 1, heights of light rays in the front lens group G1 and the rear lens group G2 may decrease or minimize sizes of the front and rear lens groups G1 and G2 such that the sizes of the front and rear lens groups G1 and G2 are approximately the same. Equation 1 may define size balance of the front lens group G1 and the rear lens group G2 within the objective lens 10.

The objective lens 10 for an endoscope may satisfy Equation 2 below.

$$d_{48}/f_{fr} \leq 2.0 \qquad \text{<Equation 2>}$$

where, $d_{48}$ denotes a distance between a vertex of the second lens L2 at the image side I and a vertex of the third lens L3 at the object side O, i.e., $d4+d5+d6+d7$, and $f_{fr}$ denotes a total focal length of the objective lens 10.

In order to decrease or minimize the size of the objective lens 10, free space within the objective lens 10 may be decreased. The free space may be arranged between the front lens group G1 and the rear lens group G2 to mount a driving unit (not shown) for moving the optical element OE. By satisfying Equation 2, a space that is needed to dispose the optical element OE and a driving unit (not shown) that moves the optical element OE may be provided between the front lens group G1 and the rear lens group G2, that is, between the second lens L2 and the third lens L3. If the objective lens 10 is outside the range of Equation 2, it may be difficult to design and assemble a driving unit for moving the optical element OE.

Also, the objective lens 10 for an endoscope may satisfy Equations 3 and 4 below.

$$f_2/f_{fr} \geq 6.0 \qquad \text{<Equation 3>}$$

$$0.3 \leq f_{45}/f_2 \leq 2.5 \qquad \text{<Equation 4>}$$

where, $f_2$ denotes a focal length of the second lens L2, $f_{fr}$ denotes a total focal length of the objective lens 10, and $f_{45}$ denotes a focal length of a doublet lens including the fourth lens L4 and the fifth lens L5.

Equations 3 and 4 may define the optical power distribution between the third lens L3 and the cemented fourth lens L4 and fifth lens L5 with the second lens L2. By satisfying Equations 3 and 4, aberration of the objective lens 10 may be corrected, thereby obtaining a high resolution image. By satisfying Equation 3, coma of a wide angle field may be corrected, and by satisfying Equation 4, coma and chromatic aberration of the objective lens 10 may be corrected.

An aspherical surface may be defined as follows. An aspheric form of an aspherical lens included in the objective lens 10 for an endoscope may be expressed by Equation 5 below, by assuming that an x-axis direction is an optical axis direction, a y-axis is a direction perpendicular to the optical axis direction, and a proceeding direction of light rays is a positive direction. In Equation 5, x denotes a distance from a vertex of a lens in the optical axis direction; and y denotes a distance from a vertex of a lens in the direction perpendicular to the optical axis direction; K denotes a conic constant; A, B, C, and D denote aspheric coefficients; and c denotes an inverse number (1/R) of a curvature radius with respect to a vertex of a lens.

$$x = \frac{cy^2}{1+\sqrt{1-(K+1)c^2y^2}} + Ay^4 + By^6 + Cy^8 + Dy^{10} \qquad \text{⟨Equation 5⟩}$$

According to exemplary embodiments of the present general inventive concept, the objective lens 10 for an endoscope that is compact and may be manufactured at low costs may be formed according to various designs as will be described below.

Hereinafter, when the objective lens 10 is focused on a distant object, $f_{fr}$ denotes a back focal length for the distant object of the entire objective lens 10; $Fno_{fr}$ denotes an F-number for the distant object; and $2\omega_{fr}$ denotes an angle of view for the distant object. Also, when the objective lens 10 is focused on a near object, $f_{nr}$ denotes a back focal length for the near object of the entire objective lens 10, $Fno_{nr}$ denotes an F-number for the near object; and $2\omega_{nr}$ denotes an angle of view for the near object. Also, R denotes a curvature radius, dn (n is a natural number) denotes a central thickness of a lens or a distance between lenses, and Nd denotes a refractive index, and Vd denotes an Abbe number. Also, Ob denotes an object surface, ST denotes a stop, and Asph denotes an aspheric surface. Lenses of each lens group are denoted with the same reference numerals in the drawings, and sn (n is a natural number) denotes a surface number of a lens. For example, from the surface of the object Ob to the image I, the first lens L1 has surfaces s1 and s2, the second lens L2 has surfaces s3 and s4, the stop is designated as s5, the optical element OE has surfaces s6 and s7, the third lens L3 has surfaces s8 and s9, the fourth lens L4 has surfaces s10 and s11, the fifth lens L5 has surfaces s11 and s12, and the cover glass CG has surfaces s13 and s14. A unit of distance is expressed in mm, and a unit of an angle of view is expressed in degrees.

FIG. 1 illustrates an objective lens 10 for an endoscope according to exemplary embodiments of the present general inventive concept. Design data of the objective lens 10 shown in FIG. 1 is as below.

TABLE 1

| | $f_{fr}$: 0.88 | $Fno_{fr}$: 4.11 | $2\omega_{fr}$: 132.3° | |
| | $f_{nr}$: 0.84 | $Fno_{nr}$: 4.13 | $2\omega_{nr}$: 137.6° | |
| Lens surface | Curvature radius (R) | Thickness (dn) | Nd | Vd |
| --- | --- | --- | --- | --- |
| Ob | | D0 | | |
| s1 | 18.20 | 0.50 | 1.8061 | 40.90 |
| s2 | 1.10 | 0.89 | | |
| s3 | −2.58 | 0.98 | 1.8467 | 23.80 |
| s4 | −2.15 | 0.90 | | |
| s5 (ST) | INFINITY | 0.20 | | |
| s6 | INFINITY | 0.60 | N6 | V6 |
| s7 | INFINITY | 0.90 | | |
| s8 | 31.50 | 1.24 | 1.8348 | 42.73 |
| s9 | −2.86 | 0.10 | | |
| s10 | 3.10 | 1.57 | 1.7880 | 47.35 |
| s11 | −2.10 | 0.47 | 2.1540 | 17.15 |
| s12 | INFINITY | 1.02 | | |
| s13 | INFINITY | 0.60 | 1.5168 | 64.17 |
| IMG | INFINITY | | | |

Table 2 below shows data regarding the optical element OE when performing focusing at a far distance and focusing at a near distance.

TABLE 2

| | Focusing at far distance | Focusing at near distance |
| --- | --- | --- |
| D0 | 9.0 | 6.0 |
| N6 | 2.0052 | 1.0 (AIR) |
| V6 | 21.00 | — (AIR) |

Figure 3A:
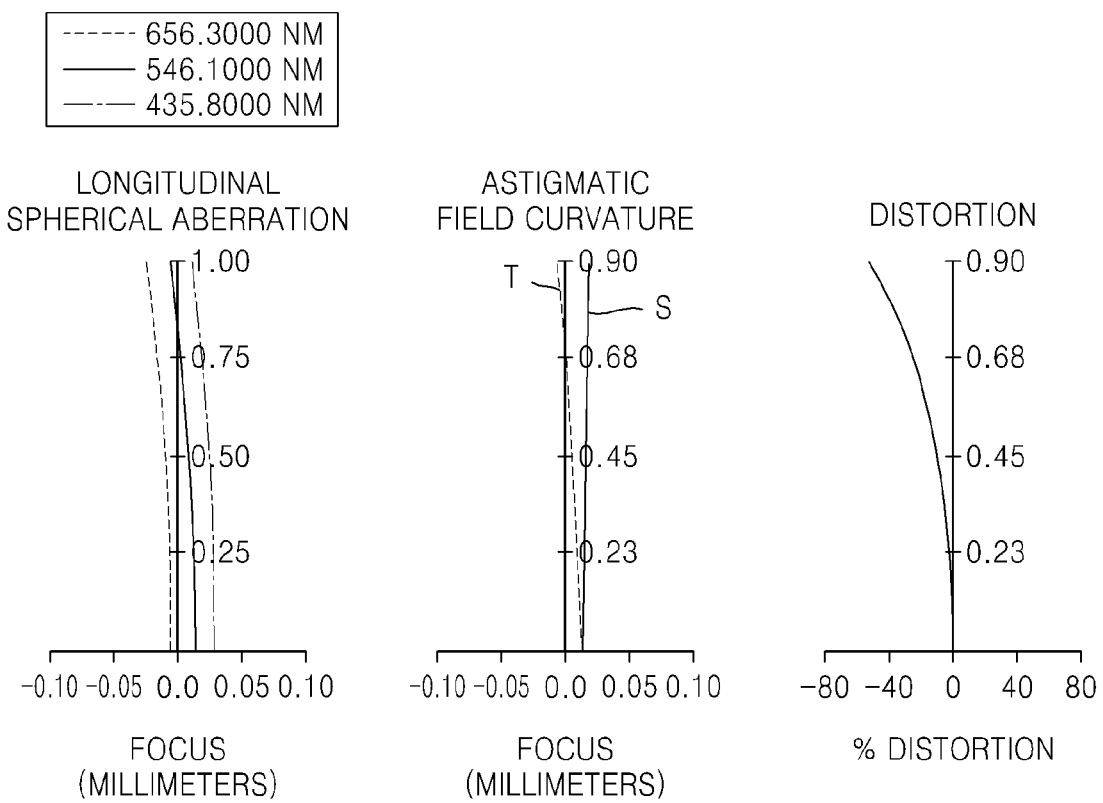
FIG. 3A illustrates aberrations when the objective lens of FIG. 1 for an endoscope performs focusing on a distant object.

FIGS. 3A and 3B show spherical aberration, astigmatic field curvature, and distortion of the objective lens 10 for an endoscope according to FIG. 1 when focusing at far distance and when focusing at near distance, respectively. As astigmatic field curvature, tangential field curvature (T) and sagittal field curvature (S) are shown.

Figure 4:
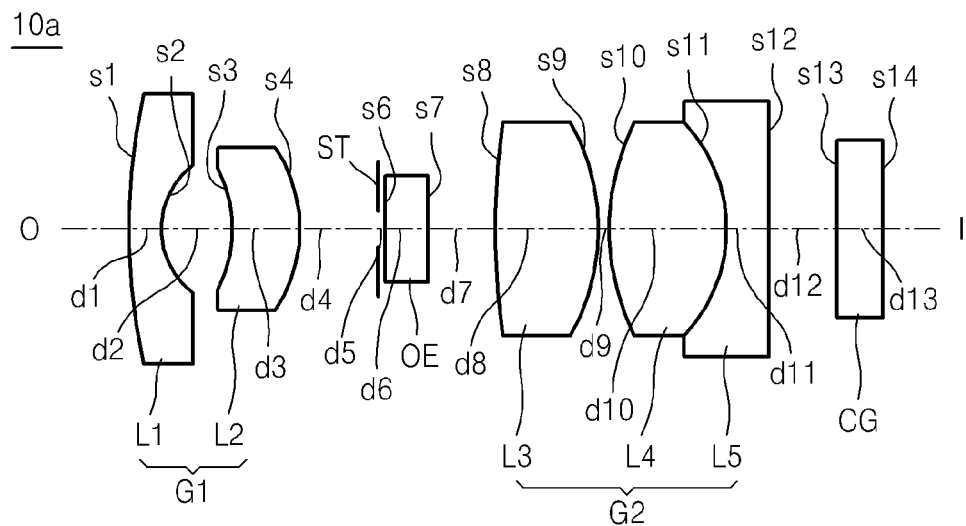
FIG. 4 is a cross-sectional view of an objective lens for an endoscope according to another embodiment of the present general inventive concept.

FIG. 4 illustrates an objective lens 10a for an endoscope according to exemplary embodiments of the present general inventive concept, and Table 3 below shows design data of the objective lens 10a of FIG. 4.

TABLE 3

| | $f_{fr}$: 0.81 | $Fno_{fr}$: 4.1 | $2\omega_{fr}$: 140.8° | |
| | $f_{nr}$: 0.78 | $Fno_{nr}$: 3.9 | $2\omega_{nr}$: 146.8° | |
| Lens surface | Curvature radius (R) | Thickness | Nd | Vd |
| --- | --- | --- | --- | --- |
| Ob | | D0 | | |
| s1 | 8.00 | 0.40 | 1.8866 | 34.95 |
| s2 | 1.02 | 0.95 | | |
| s3 | −2.23 | 0.92 | 1.6889 | 31.12 |
| s4 | −1.85 | 0.90 | | |
| S5 (ST) | INFINITY | 0.20 | | |
| s6 | INFINITY | 0.60 | N6 | V6 |
| s7 | INFINITY | 0.90 | | |
| s8 | 11.76 | 1.38 | 1.7720 | 49.98 |
| s9 | −2.90 | 0.10 | | |
| s10 | 2.96 | 1.60 | 1.7720 | 49.98 |
| s11 | −2.00 | 0.54 | 2.1540 | 17.15 |
| s12 | INFINITY | 0.92 | | |
| s13 | INFINITY | 0.60 | 1.5168 | 64.17 |
| IMG | INFINITY | | | |

Table 4 below shows data regarding the optical element OE when performing focusing at a far distance and focusing at a near distance.

TABLE 4

| | Focusing at far distance | Focusing at near distance |
| --- | --- | --- |
| D0 | 9.0 | 5.0 |
| N6 | 2.0170 | 1.0 (AIR) |
| V6 | 20.83 | — (AIR) |

Figure 5A:
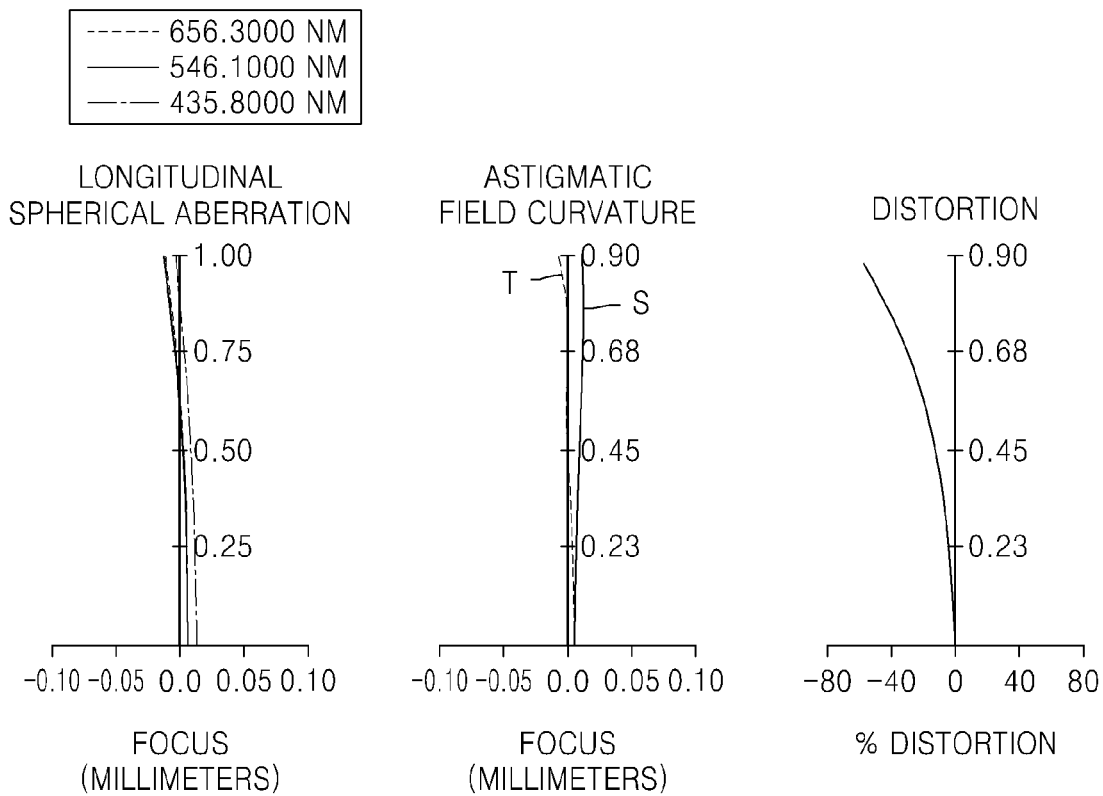
FIG. 5A illustrates aberrations when the objective lens of FIG. 4 for an endoscope performs focusing on a distant object.
Figure 5B:
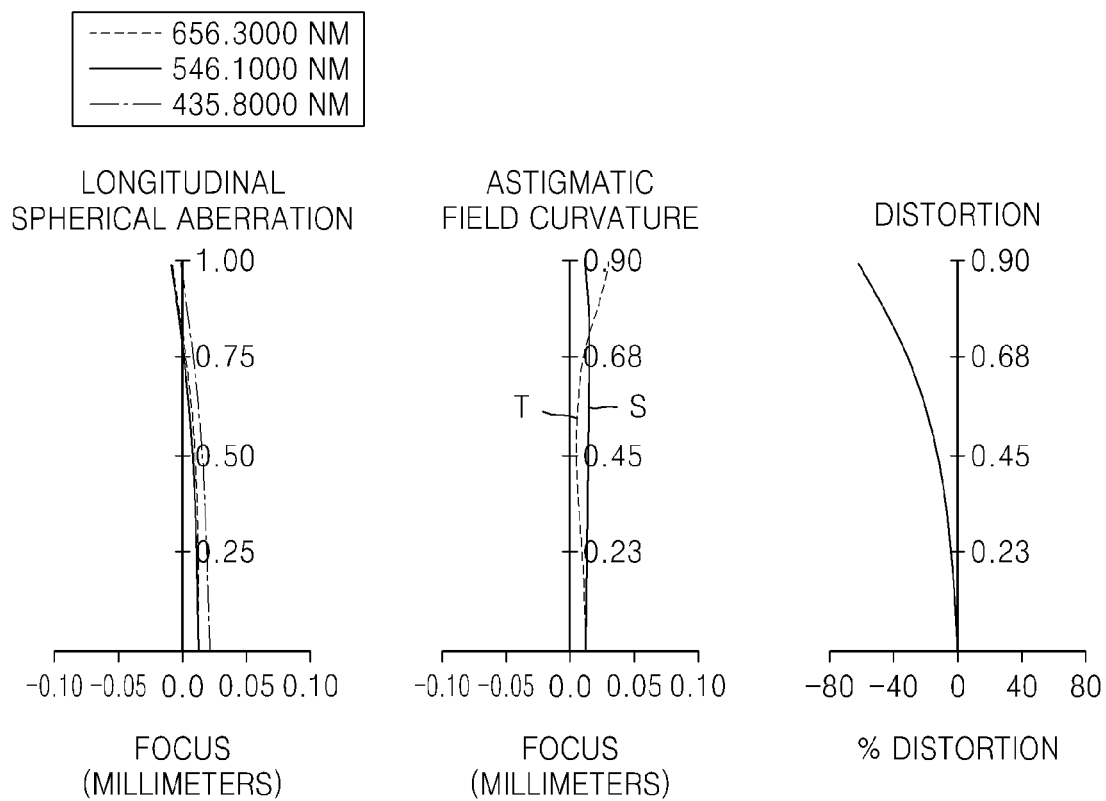
FIG. 5B illustrates aberrations when the objective lens of FIG. 4 for an endoscope performs focusing on a near object.

FIGS. 5A and 5B show spherical aberration, astigmatic field curvature, and distortion of the objective lens 10a for an endoscope according to the embodiment of FIG. 4 when focusing at far distance and when focusing at near distance, respectively.

Figure 6:
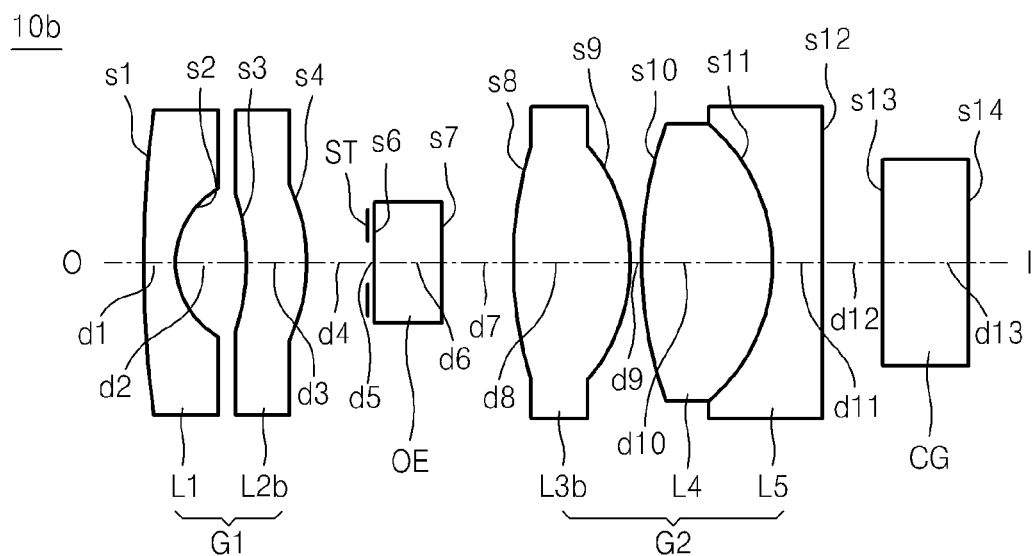
FIG. 6 is a cross-sectional view of an objective lens for an endoscope according to another embodiment of the present general inventive concept.

FIG. 6 illustrates an objective lens 10b for an endoscope according to exemplary embodiments of the present general inventive concept, and Table 5 below shows design data of the objective lens 10a of FIG. 5. A second lens L2b and a third lens L3b of the objective lens 10b are aspherical lenses. Also, the second lens L2b and the third lens L3b may be formed of a plastic.

TABLE 5

| | $f_{fr}$: 0.83 | $Fno_{fr}$: 4.0 | $2\omega_{fr}$: 140.0° | |
| | $f_{nr}$: 0.77 | $Fno_{nr}$: 3.8 | $2\omega_{nr}$: 149.0° | |
| Lens surface | Curvature radius (R) | Thickness | Nd | Vd |
| --- | --- | --- | --- | --- |
| Ob | | D0 | | |
| s1 | 14.00 | 0.40 | 1.7720 | 49.98 |
| s2 | 1.01 | 0.78 | | |
| s3 (Asph.) | −2.64 | 0.70 | 1.5855 | 29.91 |
| s4 (Asph.) | −2.43 | 0.75 | | |
| s5 (ST) | INFINITY | 0.05 | | |
| s6 | INFINITY | 0.80 | N6 | V6 |
| s7 | INFINITY | 0.85 | | |
| s8 (Asph.) | 3.98 | 1.35 | 1.5364 | 57.10 |
| s9 (Asph.) | −1.60 | 0.10 | | |
| s10 | 4.45 | 1.52 | 1.7720 | 49.98 |
| s11 | −2.15 | 0.60 | 2.1540 | 17.15 |
| s12 | INFINITY | 0.69 | | |
| s13 | INFINITY | 1.00 | 1.5225 | 62.22 |
| IMG | INFINITY | | | |

Table 6 below shows aspheric coefficients of surfaces s3 and s4 of the second lens L2b and surfaces s8 and s9 of the third lens L3b of the objective lens 10b for an endoscope according to FIG. 6.

TABLE 6

| Aspherical surface | K | A | B | C | D |
|---|---|---|---|---|---|
| Asph. 3 | −22.1306 | 0 | 0 | 0 | 0 |
| Asph. 4 | 4.1707 | 0.4319E-01 | 0 | 0 | 0 |
| Asph. 8 | 1.8386 | −0.14085-01 | 0 | 0 | 0 |
| Asph. 9 | −1.0000 | 0.2507E-02 | 0.5716E-03 | 0 | 0 |

Table 7 below shows data regarding the optical element OE when focusing at a far distance and focusing at a near distance.

TABLE 7

| | Focusing at far distance | Focusing at near distance |
|---|---|---|
| D0 | 10.0 | 4.0 |
| N6 | 1.5168 | 1.0 (AIR) |
| V6 | 64.17 | — (AIR) |

Figure 7A:
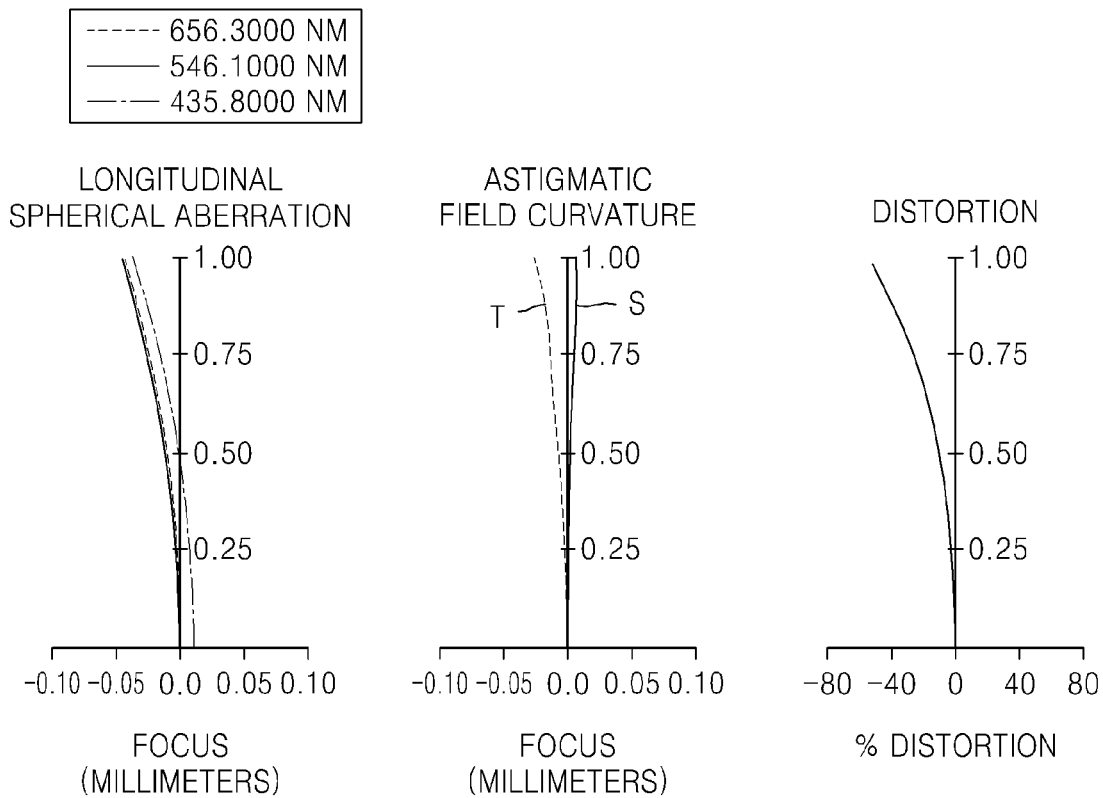
FIG. 7A illustrates aberrations when the objective lens of FIG. 6 for an endoscope performs focusing on a distant object.
Figure 7B:
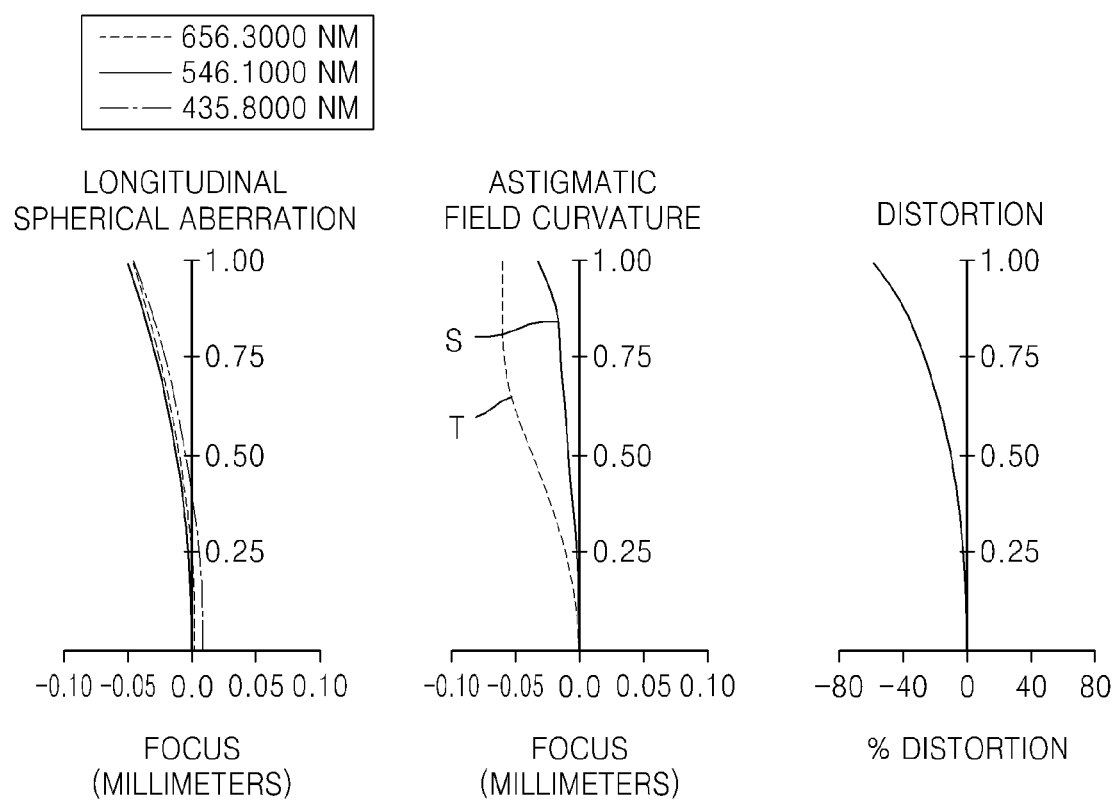
FIG. 7B illustrates aberrations when the objective lens of FIG. 6 for an endoscope performs focusing on a near object.

FIGS. 7A and 7B show spherical aberration, astigmatic field curvature, and distortion of the objective lens 10b for an endoscope according to the embodiment of FIG. 6 when focusing at far distance and when focusing at near distance, respectively.

Figure 8:
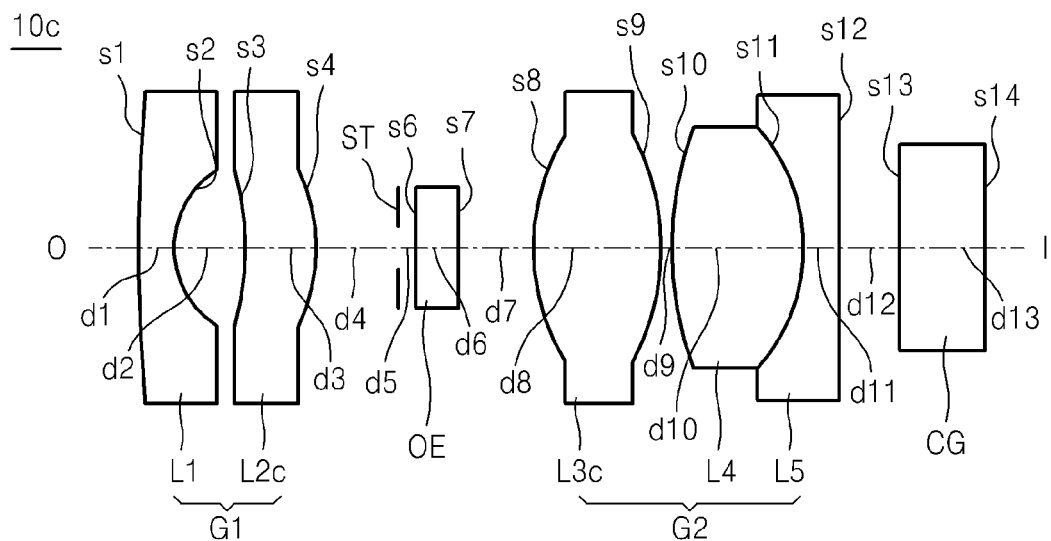
FIG. 8 is a cross-sectional view of an objective lens for an endoscope according to another embodiment of the present general inventive concept.

FIG. 8 illustrates an objective lens 10c for an endoscope according to exemplary embodiments of the present general inventive concept, and Table 8 below shows design data of the objective lens 10c of FIG. 8. A second lens L2c and a third lens L3c of the objective lens 10 are aspherical lenses. Also, the second lens L2c and the third lens L3c may be formed of a plastic.

TABLE 8

| Lens surface | $f_{fr}$: 0.78  $f_{nr}$: 0.75  Curvature radius (R) | $Fno_{fr}$: 4.0  $Fno_{nr}$: 4.0  Thickness | $2\omega_{fr}$: 140.9°  $2\omega_{nr}$: 147.3°  Nd | Vd |
|---|---|---|---|---|
| Ob | | D0 | | |
| s1 | 22.20 | 0.40 | 1.7720 | 49.98 |
| s2 | | 1.07 | | 0.84 |
| s3 (Asph.) | −2.00 | 0.80 | 1.5855 | 29.91 |
| s4 (Asph.) | −2.16 | 0.95 | | |
| s5 (ST) | INFINITY | 0.20 | | |
| s6 | INFINITY | 0.50 | N6 | V6 |
| s7 | INFINITY | 0.90 | | |
| s8 (Asph.) | 4.87 | 1.47 | 1.5364 | 57.10 |
| s9 (Asph.) | −2.04 | 0.10 | | |
| s10 | 3.90 | 1.50 | 1.7720 | 49.98 |
| s11 | −2.10 | 0.45 | 2.1540 | 17.15 |
| s12 | INFINITY | 0.68 | | |
| s13 | INFINITY | 1.00 | 1.5168 | 64.17 |
| IMG | INFINITY | | | |

Table 9 below shows aspheric coefficients of surfaces s3 and s4 of the second lens L2c and surfaces s8 and s9 of the third lens L3c of the objective lens 10c for an endoscope of FIG. 8.

TABLE 9

| Aspherical surface | K | A | B | C | D |
|---|---|---|---|---|---|
| Asph. 3 | −12.7200 | 0 | 0 | 0 | 0 |
| Asph. 4 | −12.4792 | −0.6370E-01 | 0.3504E-02 | 0 | 0 |
| Asph. 8 | 1.7550 | −0.76790-02 | 0 | 0 | 0 |
| Asph. 9 | −4.0780 | −0.2709E-01 | 0.1546E-01 | 0 | 0 |

Table 10 below shows data regarding the optical element OE when focusing at a far distance and focusing at a near distance.

TABLE 10

| | Focusing from far distance | Focusing from near distance |
|---|---|---|
| D0 | 9.0 | 5.0 |
| N6 | 1.5168 | 1.0 (AIR) |
| V6 | 64.17 | — (AIR) |

Figure 9A:
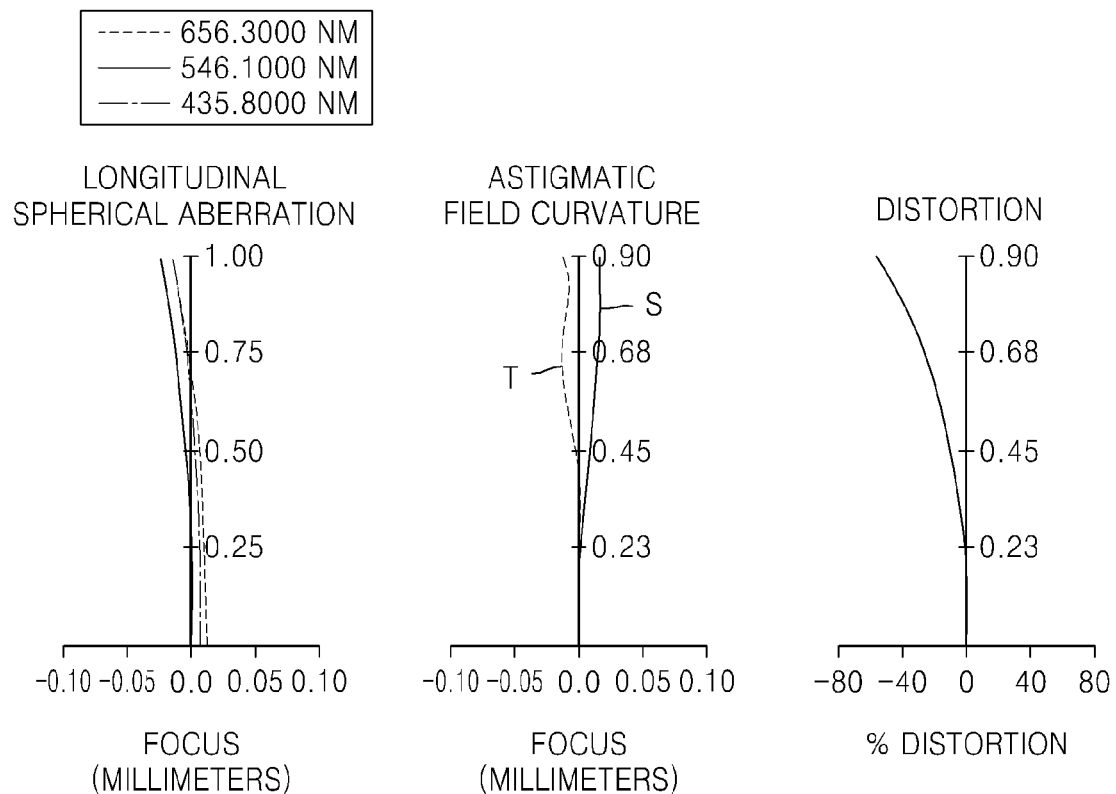
FIG. 9A illustrates aberrations when the objective lens of FIG. 8 for an endoscope performs focusing on a distant object.
Figure 9B:
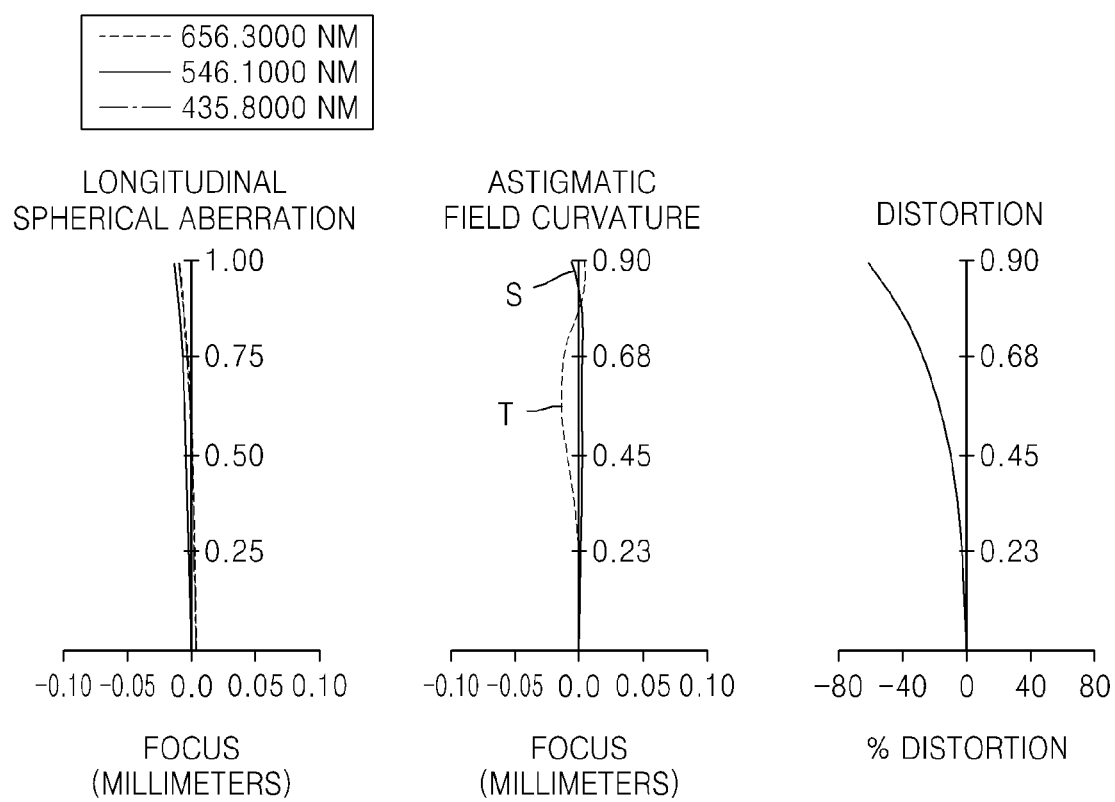
FIG. 9B illustrates aberrations when the objective lens of FIG. 8 for an endoscope performs focusing on a near object.

FIGS. 9A and 9B show spherical aberration, astigmatic field curvature, and distortion of the objective lens 10c for an endoscope according to FIG. 8 when focusing from far distance and when focusing from near distance, respectively.

Figure 10:
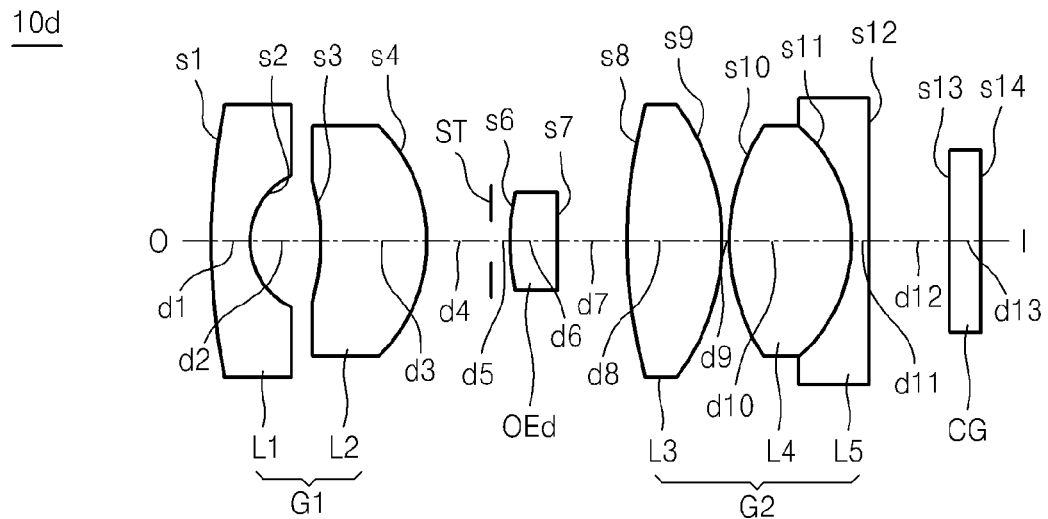
FIG. 10 is a cross-sectional view of an objective lens for an endoscope according to another embodiment of the present general inventive concept.
Figure 11A:
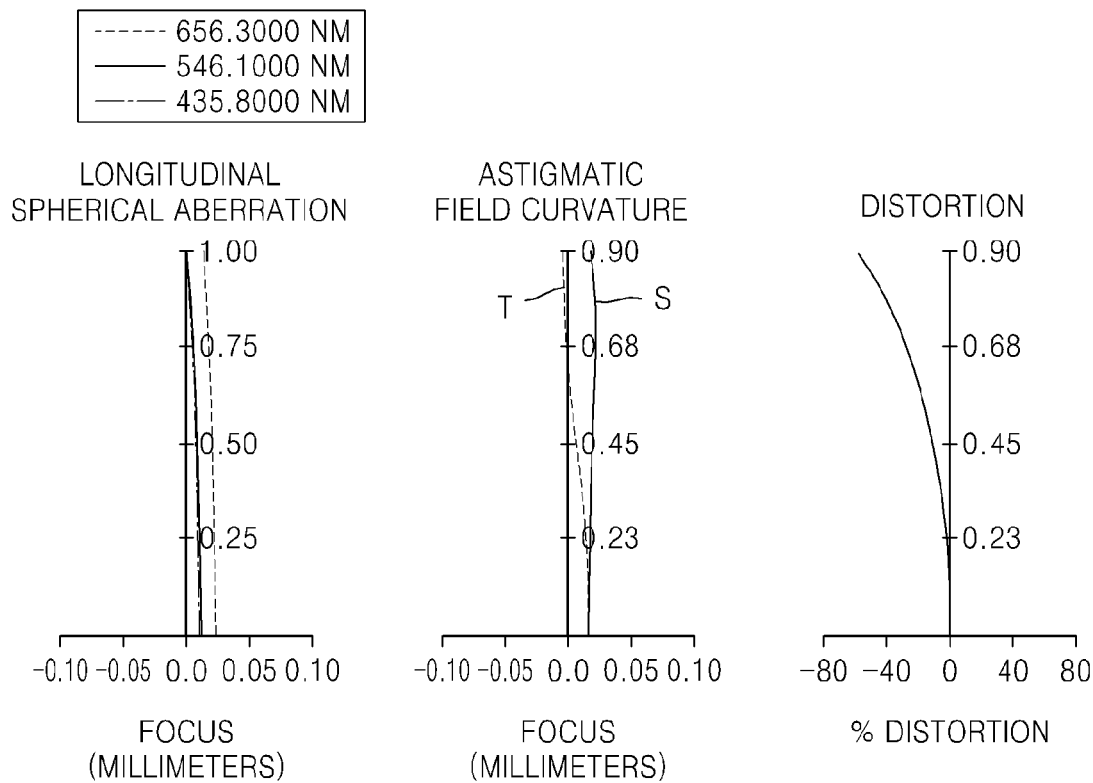
FIG. 11A illustrates aberrations when the objective lens of FIG. 10 for an endoscope performs focusing on a distant object.
Figure 11B:
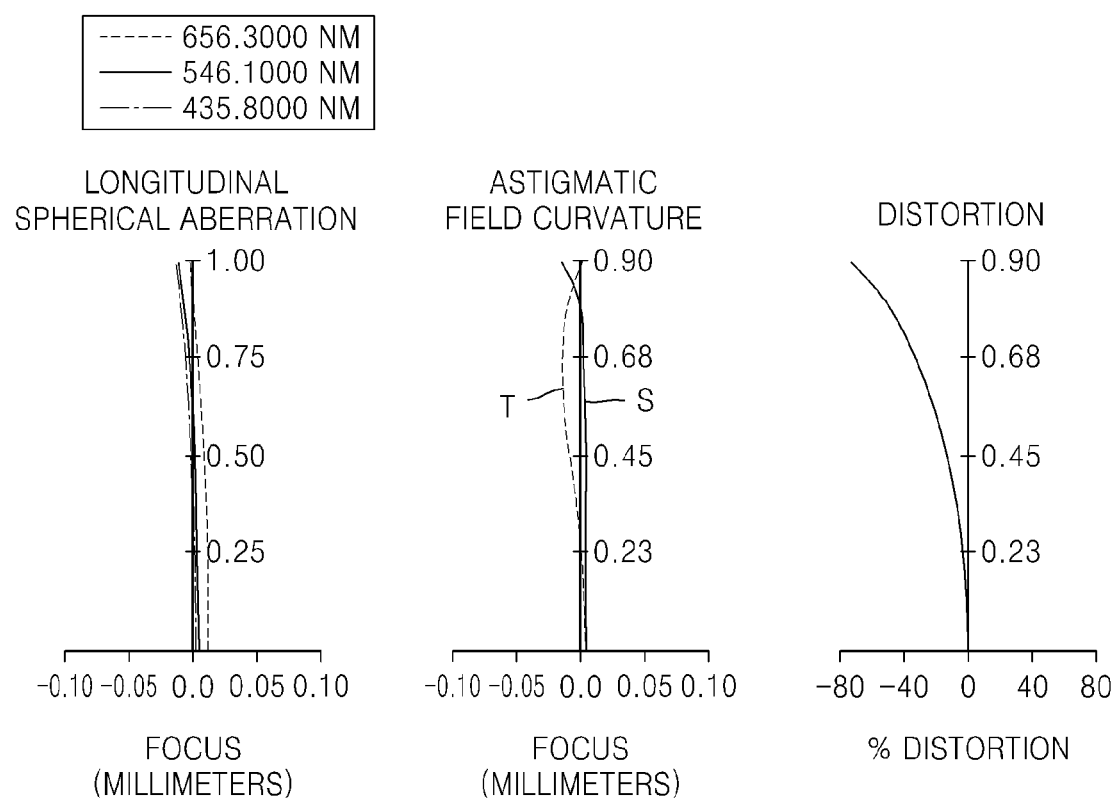
FIG. 11B illustrates aberrations when the objective lens of FIG. 10 for an endoscope performs focusing on a near object.

FIG. 10 illustrates an objective lens 10d for an endoscope according to exemplary embodiments of the present general inventive concept, and Table 11 below shows design data of the objective lens 10d of FIG. 10. According to the objective lens 10d for an endoscope, an optical element OEd has power (refractive power). For example, the optical element OEd may have a meniscus shape, for example, having a convex surface disposed toward an object side of the objective lens 10d. Also, the optical element OEd may have a positive refractive power.

TABLE 11

| Lens surface | $f_{fr}$: 0.83  $f_{nr}$: 0.77  Curvature radius (R) | $Fno_{fr}$: 4.4  $Fno_{nr}$: 4.1  Thickness | $2\omega_{fr}$: 140.0°  $2\omega_{nr}$: 149.2°  Nd | Vd |
|---|---|---|---|---|
| Ob | | D0 | | |
| S1 | 10.16 | 0.50 | 1.8886 | 33.84 |
| S2 | | 0.99 | | 0.91 |
| S3 | −2.80 | 1.38 | 1.8506 | 41.62 |
| S4 | | −2.15 | | 0.90 |
| s5 (ST) | INFINITY | 0.20 | | |
| S6 | 6.36 | 0.60 | N6 | V6 |
| S7 | 6.19 | 0.90 | | |
| S8 | 7.07 | 1.25 | 1.6657 | 57.51 |
| S9 | −3.04 | 0.10 | | |
| S10 | 2.88 | 1.55 | 1.7720 | 49.98 |
| S11 | −2.00 | 0.25 | 2.1540 | 17.15 |
| S12 | INFINITY | 1.06 | | |
| S13 | INFINITY | 0.40 | 1.5168 | 64.17 |
| IMG | INFINITY | | | |

Table 12 below shows data regarding the optical element OEd when focusing from a far distance and focusing from a near distance.

TABLE 12

| | Focusing from far distance | Focusing from near distance |
|---|---|---|
| D0 | 9.0 | 5.0 |
| N6 | 1.9211 | 1.0 (AIR) |
| V6 | 22.42 | — (AIR) |

Table 13 below shows that the objective lenses 10, 10a, 10b, 10c, and 10d satisfy Equations 1 through 4.

TABLE 13

| | objective lens 10 | objective lens 10a | objective lens 10b | objective lens 10c | objective lens 10d |
|---|---|---|---|---|---|
| Equation 1 | 1.06 | 1.20 | 1.48 | 1.68 | 0.91 |
| Equation 2 | 2.97 | 2.11 | 2.97 | 2.16 | 2.05 |
| Equation 3 | 8.40 | 6.38 | 28.01 | 45.2 | 6.57 |
| Equation 4 | 1.17 | 1.14 | 2.35 | 0.44 | 1.54 |

An objective lens for an endoscope according to exemplary embodiments of the present general inventive concept is compact and may be manufactured at low costs. In addition, focusing may be performed easily by moving the optical element OE in a direction different from the optical axis. Also, by performing focusing, endoscope images having a high resolution and a high quality may be obtained. In addition, a wide DOF of the objective lens may be provided at a near distance, thereby obtaining high quality images at a near distance. Moreover, there is an overlapping section in the range of the DOF at a near distance and the range of the DOF at a far distance, and thus clear, high quality images may be obtained more stably at a near distance.

Next, an actuator 100 that moves the optical element OEe to perform focusing of the objective lens for an endoscope according to exemplary embodiments of the present general inventive concept will be described with reference to FIG. 12. The actuator 100 of FIG. 12 may be an example of the driving unit that moves the optical element OE to focus the objective lens for an endoscope described above.

Figure 12:
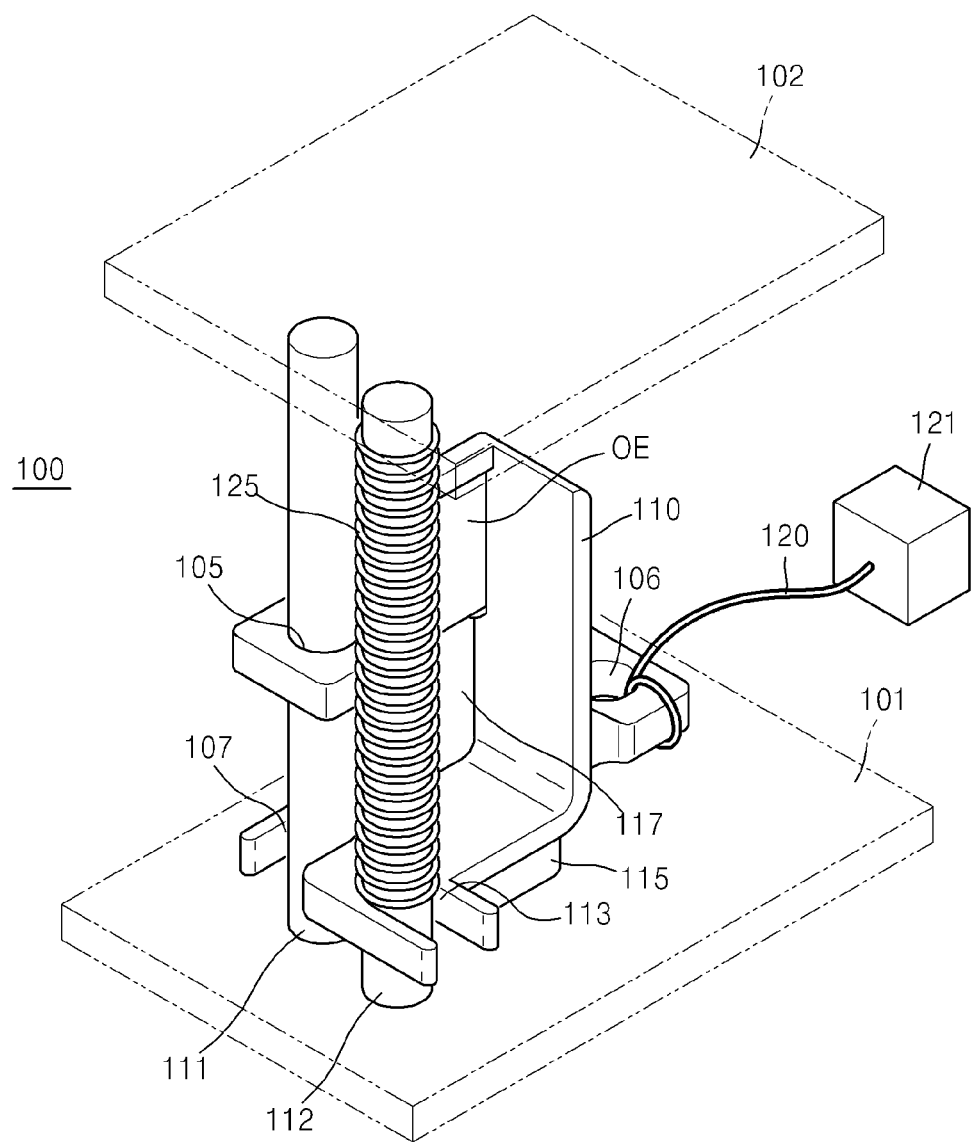
FIG. 12 is a schematic view of an actuator for focusing according to exemplary embodiments of the present general inventive concept.

Referring to FIG. 12, the actuator 100 may include a holder 110 that is movable and supports an optical element OEe, at least one guide hole formed in the holder 110, and a guide shaft that is inserted into the at least one guide hole and guides movement of the holder 110. A hole 117 is formed in a central portion of the holder 110, and the optical element OEe is mounted in a portion of the hole 117. A support threshold 115 may be further disposed on a lower surface of the holder 110. The at least one guide hole may include first through third guide holes 105, 107, and 113 formed at a side of the holder 110. The first guide hole 105 and the second guide hole 107 may be formed along the same line, and the first guide shaft 111 may be mounted in the first guide hole 105 and the second guide hole 107. The second guide shaft 112 may be mounted in the third guide hole 113. The first through third guide holes 105, 107, and 113 may be formed to have various shapes such as a circle, a U-shape, or an opened shape. The first guide shaft 111 and the second guide shaft 112 are disposed between a first plate 101 and a second plate 102 that are disposed to face each other, and the holder 110 may move in a vertical direction along the first and second guide shafts 111 and 112, i.e., the holder 110 may move in a direction parallel to the longitudinal axes of the first and second guide shafts 111 and 112. An elastic member 125 may be disposed around the second guide shaft 112, and the elastic member 125 may be a compression spring. When the holder 110 is moved upward and a force applied to the holder 110 is no longer applied, the holder 110 may return to the original position due to the elastic force of the elastic member 125.

Meanwhile, a driving unit 121 for moving the holder 110 may be included in the holder 110. The driving unit 121 may include a wire 120 to pull the holder 110. The wire 120 may be threaded through a hole 106 in the holder 110 or in a member connected to the holder 110. The wire 120 may be pulled by the hand or by using a machine or motor. When the holder 110 does not move, the optical element OEe may be disposed on the optical axis of the lenses of the objective lens, and thus, a focus may be adjusted for a far distance as shown in FIG. 2A. When the holder 110 moves upward by using the driving unit 121, the optical element OEe moves upward and may, for example, deviate from the optical axis of the objective lens. In this case, focusing may be adjusted at a near distance as shown in FIG. 2B.

As described above, by moving the optical element OEe using the actuator 100 having a simple structure, focusing of the objective lens for an endoscope may be performed. The actuator 100 illustrated in FIG. 12 is an example, and an actuator for moving the optical element OEe may have various structures.

Figure 13:
FIG. 13 is a schematic view of an endoscope system including an objective lens according to exemplary embodiments of the present general inventive concept.

Next, FIG. 13 is a schematic view of an endoscope system 200 including an objective lens 10 for an endoscope according to embodiments of the present general inventive concept.

The endoscope system 200 includes a bending portion 220 including an objective lens 10f disposed at a tip 210 at a terminal end of the bending portion 220, and an inserting portion 230 connected to the bending portion 220. The bending portion 220 may be formed of a flexible material and may bend as desired, and a shape thereof may vary according to a path along which the endoscope system 200 enters. A handle 240 for an operation such as manipulating focusing of the objective lens 10 may be included at an end of the inserting portion 230. By using the handle 240, the tip 210 may be brought near to the affected part of a patient or taken away therefrom, and an image of the affected part may be taken by using the objective lens 10f. Since the objective lens 10f has been described above, description of the objective lens 10f will be omitted here. The objective lens 10f may be any one of or any combination of the features of the objective lenses 10, 10a, 10b, 10c, and 10d as described above. By performing focusing of the objective lens 10f using a simple method, images having a high resolution and a high image quality may be obtained. FIG. 13 is a schematic view of the endoscope system 200, and the objective lens 10f may also be used in endoscope systems of other various structures.

Although a few embodiments of the present general inventive concept have been shown and described, it will be appreciated by those skilled in the art that changes may be made in these embodiments without departing from the principles and spirit of the general inventive concept, the scope of which is defined in the appended claims and their equivalents.

What is claimed is:

1. An objective lens for an endoscope, the objective lens comprising;
   a plurality of lenses;
   a stop; and
   an optical element disposed adjacent to the stop,
   wherein a focal length of the objective lens is variable according to a movement of the optical element in a direction different from an optical axis of the plurality of lenses,
   wherein a depth of field (DOF) of the objective lens is in a range from 5 mm to 100 mm at a far distance, and a DOF of the objective lens is in a range from 2.5 mm to 10 mm at a near distance.

2. The objective lens for an endoscope of claim 1, wherein the movement of the optical element is between a position on the optical axis and a position deviated from the optical axis.

3. The objective lens for an endoscope of claim 1, wherein the optical element is a non-power transparent element.

4. The objective lens for an endoscope of claim 1, wherein the optical element is a glass plate having two planar surfaces.

5. The objective lens for an endoscope of claim 1, wherein the optical element has a positive refractive power or a negative refractive power.

6. The objective lens for an endoscope of claim 1, wherein the movement of the optical element is in a direction perpendicular to the optical axis of the plurality of lenses.

7. The objective lens for an endoscope of claim 1, wherein the objective lens includes a front lens group having a negative refractive power, the stop, a rear lens group having a positive refractive power, and the optical element is disposed between the front lens group and the stop or between the stop and the rear lens group.

8. The objective lens for an endoscope of claim 1, wherein an aperture of the stop is constant.

9. An objective lens for an endoscope, the objective lens comprising;
    a plurality of lenses;
    a stop; and
    an optical element disposed adjacent to the stop,
    wherein a focal length of the objective lens is variable according to a movement of the optical element in a direction different from an optical axis of the plurality of lenses, and
    wherein an F-number Fno of the objective lens is in a range from 4 to 6.

10. An objective lens for an endoscope, comprising, sequentially from an object side of the objective lens,
    a front lens group having a negative refractive power,
    a stop,
    a rear lens group having a positive refractive power, and
    an optical element disposed between the front lens group and the stop or between the stop and the rear lens group,
    wherein the optical element is moveable in a direction different from an optical axis to focus the objective lens, and
    the front lens group includes a first lens having a negative refractive power and a second lens having a positive refractive power, and
    the rear lens group includes a third lens having a positive refractive power, a fourth lens having a positive refractive power, and a fifth lens having a negative refractive power,
    wherein the objective lens satisfies the following equation:

$$0.8 \leq |d_s/f_{G1}| \leq 1.8$$

where $d_s$ denotes a distance between a vertex of the first lens at the object side and the stop, and $f_{G1}$ denotes a focal length of the front lens group.

11. The objective lens for an endoscope of claim 10, wherein the second lens is a meniscus type lens having a convex surface disposed toward an image side of the objective lens.

12. The objective lens for an endoscope of claim 10, wherein the objective lens satisfies the following equation:

$$d_{48}/f_{fr} \geq 2.0$$

where $d_{48}$ denotes a distance between a vertex of the second lens at an image side of the objective lens and a vertex of the third lens at the object side of the objective lens, and $f_{fr}$ denotes a total focal length of the objective lens.

13. The objective lens for an endoscope of claim 10, wherein the fourth lens and the fifth lens are cemented together.

14. The objective lens for an endoscope of claim 13, wherein the objective lens satisfies the following equation:

$$f_2/f_{fr} \geq 6.0$$

$$0.3 \leq f_{45}/f_2 \leq 2.5$$

where $f_2$ denotes a focal length of the second lens, and $f_{fr}$ denotes a total focal length of the objective lens, and $f_{45}$ denotes a focal length of the cemented fourth lens and fifth lens.

15. The objective lens for an endoscope of claim 10, wherein the second lens and the third lens include aspherical surfaces.

16. The objective lens for an endoscope of claim 10, wherein a focal length is varied by the movement of the optical element is between a position on the optical axis and a position deviated from the optical axis.

17. The objective lens for an endoscope of claim 10, wherein the optical element is a non-power transparent element.

18. The objective lens for an endoscope of claim 10, wherein the optical element is a glass plate having two planar surfaces.

19. The objective lens for an endoscope of claim 10, wherein the optical element has a positive refractive power or a negative refractive power.

20. The objective lens for an endoscope of claim 10, wherein a focal length is varied the movement of the optical element in a direction perpendicular to the optical axis.

21. The objective lens for an endoscope of claim 10, wherein an F-number Fno of the objective lens is in a range from 4 to 6.

22. The objective lens for an endoscope of claim 10, wherein a depth of field (DOF) of the objective lens is in a range from 5 mm to 100 mm at a far distance, and a DOF of the objective lens is in a range from 2.5 mm to 10 mm at a near distance.

23. The objective lens for an endoscope of claim 10, wherein an aperture of the stop is constant.

24. An endoscope system comprising:
    a bending portion having a terminal end;
    an objective lens disposed at the terminal end of the bending portion; and
    an inserting portion connected to the bending portion at an end of the bending portion opposite the terminal end,
    wherein the objective lens includes a plurality of lenses, a stop, and an optical element disposed adjacent to the stop, and a focal length of the objective lens is variable according to a movement the optical element in a direction different from an optical axis of the plurality of lenses, and
    wherein a depth of field (DOF) of the objective lens is in a range from 5 mm to 100 mm at a far distance, and a DOF of the objective lens is in a range from 2.5 mm to 10 mm at a near distance.

25. An endoscope system comprising:
    a bending portion having a terminal end;
    an objective lens disposed at the terminal end of the bending portion; and
    an inserting portion connected to the bending portion at an end of the bending portion opposite the terminal end,
    wherein the objective lens comprises, sequentially from an object side of the objective lens,
    a front lens group having a negative refractive power, a stop, a rear lens group having a positive refractive power, and an optical element disposed between the front lens group and the stop or between the stop and the rear lens group, wherein the optical element is moveable in a direction different from an optical axis to focus the objective lens, and the front lens group includes a first lens having a negative refractive power and a second lens having a positive refractive power, and the rear lens group includes a third lens having a positive refractive power, a fourth lens having a positive refractive power, and a fifth lens having a negative refractive power, wherein the objective lens satisfies the following equation:

$$0.8 \le |d_s/f_{G1}| \le 1.8$$

where $d_s$ denotes a distance between a vertex of the first lens at the object side and the stop, and $f_{G1}$ denotes a focal length of the front lens group.

26. The endoscope system of claim 25, wherein the endoscope system satisfies the following equation:

$$f_2/f_{fr} \ge 6.0$$

$$0.3 \le f_{45}/f_2 \le 2.5$$

where $f_2$ denotes a focal length of the second lens, and $f_{fr}$ denotes a total focal length of the objective lens, and $f_{45}$ denotes a focal length of a doublet lens including the fourth lens and the fifth lens.

27. The endoscope system of claim 25, wherein a depth of field (DOF) of the objective lens is in a range from 5 mm to 100 mm at a far distance, and a DOF of the objective lens is in a range from 2.5 mm to 10 mm at a near distance.

28. An objective lens usable with an endoscope, comprising:

a front lens group having a negative refractive power;

a rear lens group having a positive refractive power;

a stop disposed between the front and rear lens group; and an optical element disposed between the front lens group and the stop or between the stop and the rear lens group, the optical element being moveable in a direction different from an optical axis of the front lens group and the rear lens group wherein the front lens group, sequentially from an object side of the objective lens, further comprises a first lens having a negative refractive power and a second lens having a positive refractive power.

29. The objective lens of claim 28, wherein the second lens is a meniscus type lens having a convex surface disposed toward an image side of the objective lens.

30. The objective lens of claim 28, wherein the rear lens group, sequentially from an object side of the objective lens, further comprises a third lens having a positive refractive power, a fourth lens having a positive refractive power, and a fifth lens having a negative refractive power.

31. The objective lens of claim 30, wherein the second lens and the third lens include aspherical surfaces.

32. The objective lens of claim 28, wherein the rear lens group, sequentially from an object side of the objective lens, further comprises a third lens having a positive refractive power, a fourth lens having a positive refractive power, and a fifth lens having a negative refractive power.

* * * * *